United States Patent
Bloembergen et al.

(10) Patent No.: US 6,242,593 B1
(45) Date of Patent: *Jun. 5, 2001

(54) ENVIRONMENTALLY FRIENDLY SUGAR-BASED VINYL MONOMERS USEFUL IN REPULPABLE ADHESIVES AND OTHER APPLICATIONS

(75) Inventors: Steven Bloembergen, Okemos; Ian J. McLennan, Lansing; Ramani Narayan, Okemos, all of MI (US)

(73) Assignee: Ecosynthetix Inc., Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/145,937

(22) Filed: Sep. 3, 1998

Related U.S. Application Data

(62) Division of application No. 08/920,911, filed on Aug. 29, 1997, now Pat. No. 5,872,199.

(51) Int. Cl.⁷ ............................................. C07H 1/00
(52) U.S. Cl. ................. 536/123.1; 536/123.13; 536/124; 536/126
(58) Field of Search .................... 536/123.1, 123.13, 536/124, 126

(56) References Cited

U.S. PATENT DOCUMENTS

| | | |
|---|---|---|
| 3,839,318 | 10/1974 | Mansfield . |
| 4,713,436 | 12/1987 | Downs et al. . |
| 4,714,634 | 12/1987 | Miyazono et al. . |
| 4,806,275 | 2/1989 | Johnson et al. . |
| 5,166,337 | 11/1992 | Ripke . |
| 5,266,690 | 11/1993 | McCurry, Jr. et al. . |
| 5,449,763 | 9/1995 | Wulff et al. . |
| 5,580,940 | 12/1996 | Oosterhoff . |
| 5,597,654 | 1/1997 | Scholz et al. . |
| 5,756,072 | 5/1998 | Beck et al. . |
| 5,872,199 | * 2/1999 | Bloembergen . |

FOREIGN PATENT DOCUMENTS

| | | |
|---|---|---|
| 0 738 737 A2 | 10/1996 | (EP) . |
| 1 444 874 | 8/1976 | (GB) . |
| WO 90/07516 | 7/1990 | (WO) . |
| WO 96/07516 | 7/1990 | (WO) . |

OTHER PUBLICATIONS

M. Biermann, et al., "Alkylpolyglucoside—Technologie und Eigenshaften," *starch/stärke* 45(8):281–288, 1993.

Steven Bloembergen, et al., "Polymer Resins Designed for Environmental Sustainability," *Adhesives Age*, Feb. 1998.

* cited by examiner

*Primary Examiner*—James O. Wilson
(74) *Attorney, Agent, or Firm*—Quarles & Brady LLP

(57) ABSTRACT

Copolymers prepared from novel alkyl polyglycoside maleic acid esters and vinyl monomers are biodegradable and repulpable and are useful in adhesives, coatings, sizing agents, toners, retention aids and related polymer resins in paper and paperboard applications, in wood gluing, packaging and other applications.

7 Claims, No Drawings

ENVIRONMENTALLY FRIENDLY SUGAR-BASED VINYL MONOMERS USEFUL IN REPULPABLE ADHESIVES AND OTHER APPLICATIONS

CROSS REFERENCE TO RELATED APPLICATION

This application is a divisional application of U.S. patent application Ser. No. 08/920,911, filed Aug. 29, 1997, now U.S. Pat. No. 5,872,199.

FIELD OF THE INVENTION

The present invention relates to novel alkyl polyglycoside maleic acid esters and corresponding copolymers useful in adhesives, coatings and other applications. More particularly, it relates to sugar based vinyl monomers and to copolymers useful in repulpable and adhesives.

BACKGROUND OF THE INVENTION

Polymeric adhesives and paper coatings are used in many disposable packaging applications. Numerous adhesives and glossy coatings are used in the packaging of products such as salt, sugar, tea, coffee and bottle labels, etc. All of these products, and numerous other packaging materials end up for the most part in municipal solid waste (MSW) streams in landfills. Paper and paperboard represent a significant component (~35% by volume) of the MSW stream and efforts are underway to recycle certain streams and compost others. These largely cellulosic packaging materials should be compatible with composting or paper recycling operations.

With the rising cost of virgin fiber and the increased demand for wastepaper, the pressure is on to re-use more and more contaminated wastepaper. As a result, contaminant removal, which is essential to convert wastepaper into a reusable fiber, is one of the most important factors influencing the economics of the recycling operation, since this has a direct bearing on the yield of reusable fiber from wastepaper and its total cost. Old newsprint (ONP) is the most abundant used paper fiber source, and is most commonly used for the production of recycled paper. Efficient removal of the ink from ONP can be accomplished only by incorporating about 25 to 40% of old magazine (OMG). The OMG contains clays and mineral particles that facilitate the removal of the ink by a flotation de-inking process. The introduction of OMG also improves fiber strength and brightness levels of the recycled fiber. On the other hand, the incorporation of OMG in the recycling process introduces polymer residues from the adhesives and coatings used to manufacture the magazines.

To benefit the environment, adhesives and other polymeric resins used in paper and paperboard applications should be repulpable and not interfere with the recycling process. In addition, they should be biodegradable and have the required cost and performance characteristics to compete effectively in the market place.

Various natural adhesives (starches, dextrins, etc.) and derivatives of natural products which are biodegradable and have adhesive properties, such as carboxymethyl cellulose, amylose from starch, and casein from milk find uses in adhesive applications. Natural adhesives are used in packaging applications, but they continue to be displaced by synthetics primarily due to performance. Although they are biodegradable and compostable, these natural adhesives cause a problem in paper recycling because they are water soluble, and thus are concentrated in the closed-system water loop of the repulping process where they build up in the initial section of the dryer and on the dryer felts.

With the growing trend of mills re-using their process water, it is becoming as important to effectively remove all contaminants from the pulp flow as it is to remove them totally from the water system in an effort to prevent the accumulation of colloidal impurities. The preferred approach to achieve this requirement is to separate the contaminants at the earliest possible step in the process, but the inherent sticky nature of currently used hot melts and pressure-sensitive adhesive products makes this very difficult. The reduction of water consumption (zero-discharge) with closed water recirculation systems causes reagglomeration of dispersed adhesives resulting in deposits known as "stickies" on dryer walls and on the polyester 'wire', i.e. the felt on which the recycled paper is deposited. This occurs at very high speeds, and once adhesive residues begin to deposit, build-up occurs exponentially leading to costly mill shut downs.

The residues from adhesives and other polymeric materials currently used in glossy paper coatings, sizing agents, toner particles, etc., which lead to the formation of "stickies", can have a major impact on the smooth operation and the economics of a paper recycling process. Currently, centrifugal cleaning and fine screening are regarded as the best systems for stickies removal, but these are costly and inefficient.

The commercially available adhesives which are characterized as being repulpable are generally water soluble synthetic adhesives which still cause stickies problems in closed loop recycling mills. Therefore, there is still a need for repulpable adhesives and coatings that match the performance and cost of the predominantly synthetic products now being used. A truly 'repulpable' polymer is a polymer which does not persist as "stickies" in a paper recycling process, but which can be quantitatively removed from the process using conventional equipment found in a paper recycling mill.

BRIEF SUMMARY OF THE INVENTION

It is an object of the present invention, to provide novel copolymers which are useful in biodegradable, repulpable adhesives, coatings, sizing agents, toners, retention aids and related products used in paper and paperboard applications, in wood gluing and other packaging applications.

The copolymers of the present invention are copolymers of alkyl polyglycoside maleic acid esters and vinyl monomers. The novel copolymers of the present invention may be represented by the following formula:

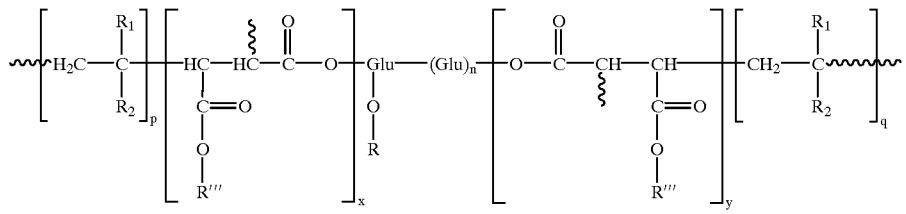

wherein Glu is a saccharide moiety which is derived from α-D-glucose (dextrose), fructose, mannose, galactose, talose, gulose, allose, altrose, idose, arabinose, xylose, lyxose, ribose, or mixtures thereof, or which can be derived by hydrolysis from the group consisting of starch, corn syrups or maltodextrins, maltose, sucrose, lactose, maltotriose, xylobiose, mellibiose, cellobiose, raffinose, stachiose, levoglucosan, and 1,6-anhydroglucofuranose. $R_1$ and $R_2$ are substituent groups of a vinyl monomer or mixture of vinyl monomers, wherein said vinyl monomer or mixture of vinyl monomers is selected from the group consisting of vinyl acetate, ethyl hexyl acrylate, butyl acrylate, ethyl acrylate, hydroxyethyl acrylate, hydroxyethyl methacrylate, lauryl acrylate, methyl methacrylate, methacryclic acid, acrylic acid, and other acrylates or mixtures of different acrylate monomers, ethylene, 1,3-butadiene, styrene, vinyl chloride, vinylpyrrolidinone, and other vinyl monomers, or mixtures thereof, R is selected from the group consisting of a C1 to C30 alkyl or a mixture thereof, more preferably a C3 to C8 alkyl or a mixture thereof, R''' is selected from the group consisting of a C1 to C30 alkyl or a mixture thereof, or a hydrogen, preferably a C8 to C18 alkyl or a mixture thereof, and most preferably a C12 to C14 alkyl or a mixture thereof; n is an integer ranging from 0 to 10, its average value ranging from 0.3 to 1; thus, <n+1>=1.3 to 2 corresponds to the average degree of oligomerization of the alkyl polyglycoside; x and y are integers ranging from 0 to 3 or from 0 to 4, where the maximum value of 3 or 4 for x and y equals the number of hydroxyls on the Glu moiety, but not both x and y are zero, and, p and q are integers ranging from 0 to 1000, but not both p and q are zero. The lines indicate continuing polymer chains.

The copolymers of the present invention are useful in adhesives, coatings, sizing agents, toners, retention aids and related polymer resins in paper and paperboard applications, in wood gluing and other packaging applications.

DETAILED DESCRIPTION OF THE INVENTION

The copolymers are prepared from alkyl polyglyosides maleic acid esters and conventional vinyl monomers.

The maleic acid esters of APG's (designer sugar molecules) have a polymerizable double bond and they are prepared by the reaction of an APG, maleic acid anhydride and alcohol. The preparation of the APG's and the maleic acid esters can be illustrated as follows:

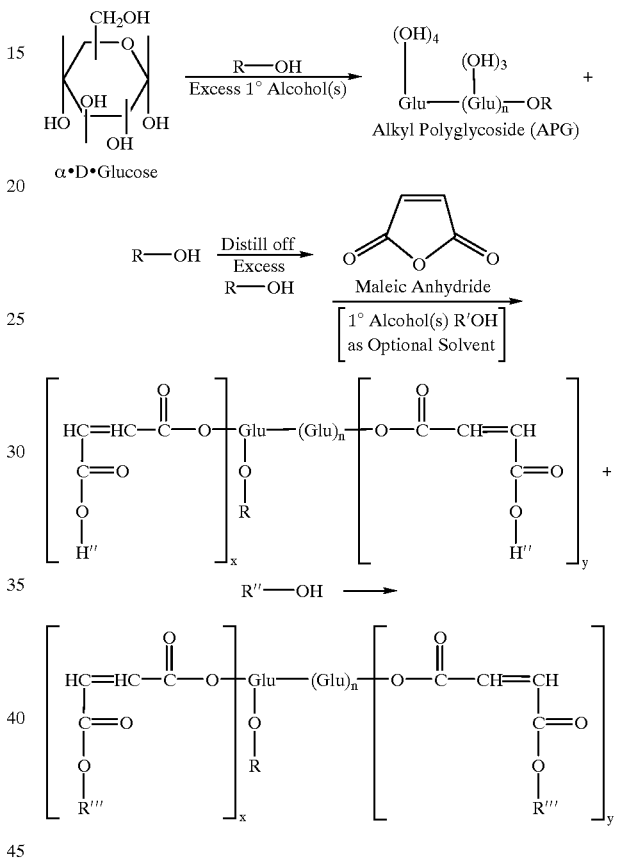

in which R" is selected from the group consisting of C1 to C30 alkyl groups or mixtures thereof, and all other symbols are as previously defined.

As illustrated above, an aldose sugar, such as α-D-glucose, is first reacted at the anomeric C1 carbon position with a primary alcohol or a mixture of primary alcohols (R—OH), to form an alkyl polyglycoside (APG). The reaction is preferably conducted in the presence of an acid catalyst, such as concentrated sulfuric acid, in accordance with known methods. The excess alcohol may be removed by vacuum distillation or by other physical separation techniques, such as extraction. The preparation of APG's is described in U.S. Pat. No. 3,839,318.

When the APG is reacted with maleic acid anhydride at temperatures from about 55° C. up to 120° C. under anhydrous and homogeneous reaction conditions a primary alcohol or a mixture of primary alcohols (R'—OH), having an alkyl group of preferably a C3 to C8 or a mixture thereof, can be added during this step as a solvent for the APG. When the alcohols R—OH and R'—OH are the same, partial removal of excess alcohol suffices in the reaction step to form the APG. The R'—OH alcohol is a reactive solvent which, upon reaction with maleic acid anhydride, provides an alkyl maleic acid monomer. Thus, this alcohol acts as a solvent during the maleation step, but is itself reacted quantitatively with maleic anhydride to provide a copolymerizable solvent/monomer in which the maleated APG is soluble. In place of the primary alcohol solvent, a dialkyl maleic ester can be used as a copolymerizable solvent, having alkyl groups of preferably a C1 to C18 alkyl or a mixture thereof, more preferably a C1 to C8 alkyl or a mixture thereof, and most preferably a C4 alkyl.

Following the maleation reaction, a primary alcohol (R"OH) or a mixture of primary alcohols, having an alkyl group of preferably C1 to C18 or a mixture thereof, more preferably C8 to C18 alkyl or a mixture thereof, and most preferably a C12 to C14 alkyl or a mixture thereof, can be added to esterify any residual unreacted maleic anhydride, a portion or all of the free acid groups of the alkyl polyglycoside maleic acid and of the alkyl maleic acid, if present.

The alcohols for use in the above process are those hydroxyl-functional organic compounds capable of alkylating a sacchride in the "1" position. The alcohols can be naturally occuring, synthetic or derived from natural sources.

The molar stoichiometry of maleic acid anhydride to APG is controlled to be more than one to afford incorporation of the sugar molecules into the polymeric structure.

The copolymers of the present invention are prepared by reacting the maleic acid esters of an APG with conventional vinyl monomers, such as vinyl acetate, ethyl hexyl acrylate, butyl acrylate, ethyl acrylate, hydroxyethyl acrylate, hydroxyethyl methacrylate, lauryl acrylate, methyl methacrylate, methacrylic acid, acrylic acid, and other acrylates or mixtures of different acrylate monomers, ethylene, 1,3-butadiene, styrene, vinyl chloride, vinylpyrrolidinone, and other vinyl monomers or mixtures thereof. Other suitable vinyl monomers include those disclosed in Table II/1–11 in Polymer Handbook, J. Bandrup, 3rd Ed. John Wiley & Sons Inc., (1989).

The use of divinyl sugar monomers produces random copolymers when reacted with conventional vinyls monomers. Randomness in the copolymers can be attained by using a monomer pre-emulsion which is slowly added to the polymerizing mixture. This so-called starve-fed copolymerization process is a process well-known to those skilled in the art.

The reaction of a maleic acid ester of an APG with a vinyl monomer to form a copolymer of the present invention may be illustrated as follows:

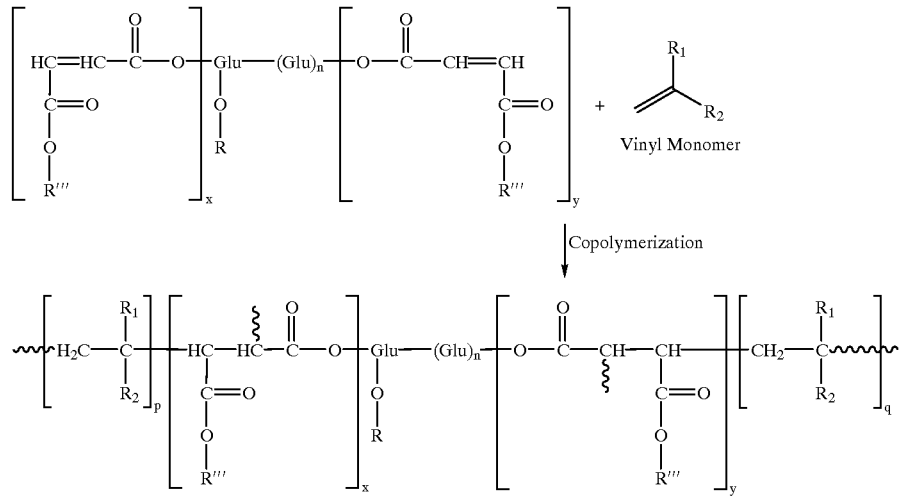

The copolymers of the present invention are water-borne dispersions which contain no volatile organic compounds (VOC's) and incorporate 'designer sugar molecules' along with conventional vinyl monomers. The conventional vinyl monomers provide the design flexibility common to current commercial synthetic copolymer resins, while the 'designer sugar molecules' provide the properties of repulpability and biodegradability.

The APG's are made from renewable resources, namely, sugars such as monosaccharides, oligosaccharides or polysaccharides. The most preferred sugar is dextrose (α-D-glucose) which is derived from corn.

The maleic acid esters of the APG's which are prepared by reacting an APG with maleic acid anhydride and subsequently with alcohol, are low-cost monomers which contain a polymerizable double bond.

The most preferred APG's for use in the present invention are those containing lower alkyl groups of four to six carbons (butyl to hexyl) or mixtures thereof, because such APG's are viscous liquids which can be readily reacted with maleic acid anhydride in the absence of a solvent. The use of butyl to hexyl polyglycosides, which are viscous liquids that can be readily reacted with maleic anhydride in the absence of a solvent, is a unique advantage of this invention.

Whereas unmodified sugar is highly polar and insoluble in most organic solvents or monomers, the APG is a viscous liquid or solid which is soluble in the organic phase to facilitate reaction with maleic acid anhydride. Above its melting point of about 55° C., maleic acid anhydride is a liquid which is miscible with the APG. This avoids the use of a solvent that would contribute to VOC's.

In addition, common sugars such as α-D-glucose, or the mono- and disaccharides, oligosaccharides and polysaccharides, generally contain appreciable levels of water (typically 8 to 12 weight %). In contrast, the APG's, which are prepared by the method described above, have a very low moisture content (typically less than 1 weight %). This is important because maleic acid anhydride is readily hydrolyzed by water to produce maleic acid as an undesired byproduct. Thus, an APG can be reacted with maleic anhydride at temperatures from about 55° C. up to 120° C. under anhydrous and homogeneous reaction conditions.

APG's having higher alkyl groups also can be used in accordance with the present invention, in combination with a primary alcohol or a mixture of primary alcohols, having an alkyl group of preferably a C4 to C18 or a mixture thereof, or a dialkyl maleic ester, as a solvent for the APG during the maleation step. The incorporation of an alcohol as a reactive and copolymerizable solvent, or a dialkyl maleic ester as a copolymerizable solvent, to facilitate the use of higher alkyl APG's is another advantage of this invention.

The molar stoichiometry of maleic anhydride to APG is controlled to be more than one to afford incorporation of the sugar molecules into the polymeric structure. The use of maleic anhydride to introduce sugar within the polymeric structure of the APG ester/vinyl copolymer chains, is a unique feature of this invention.

The copolymers are synthetic latex or suspension copolymers which contain sugar-based units that are incorporated within the polymeric structure. This is supported by the observation that dried films, prepared from latex cast on a glass substrate, were found to be transparent. The bi- or multi-functionality of the sugar-based units permits the introduction of the sugar units within the polymeric structure of the copolymer chains.

The ability to incorporate sugar units into polymeric chains results in copolymers which are susceptible to biodegradation to produce low molecular weight fragments. If enough biodegradable links are introduced into the polymer chains using 10 to 30 mole % of the APG maleic acid ester, the initial biodegradation of these copolymers leads to low molecular weight polyolefin oligomers, which in turn are biodegradable themselves provided they are aliphatic and their molecular weight is below about 1000 g/mole.

Evidence of the biodegradability of the copolymer made in accordance with the present invention was demonstrated in compost experiments which confirmed that there were increasing levels of biodegradability with increased levels of the AOC maleic acid ester (10 to 30 mole %.

Without being restrictive, it is believed that the copolymers experience an increase in surface energy as they go from a dry state in which they serve as adhesives, to a wet state when they are dispersed in water in the paper recycling process.

As previously mentioned, contaminant removal during paper recycling is of major importance owing to the increased use of closed and semi-closed loop systems in the process water. Thus, there are more problems with contaminants (such as stickies) and other dissolved colloidal substances in paper recycling mills when the process water loop is switched from an open system to a closed system. Adhesive particles can be removed from the process water by a number of different processes including forward and reverse washing, screening and flotation. The size of the contaminant particle determines to some extent the type of removal process to be used.

TABLE 2

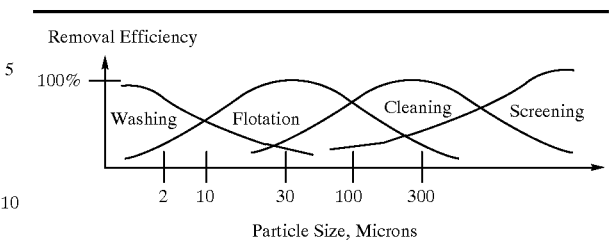

Table 2 summarizes the relative efficiencies of the various contaminant removal processes that can be used in paper recycling as a function of particle size. The narrower the size distribution, the more efficient it becomes to remove contaminants with a given process step of the paper recycling process. Thus one would like to produce an adhesive which desorbs from paper fiber under repulping conditions and is broken down to a particle size range (under shear conditions found in repulpers) in which the particles could be easily removed by one or a combination of several of the contaminant removal processes cited in Table 2. For example, for an adhesive particle to be efficiently removed by a flotation process, the particles have to be hydrophobic and in the size range of about 10 to 70 μm.

When levels of 1 to 25 mole percent of the APG maleic ester monomer are used, the copolymers are non-tacky under repulping conditions, and doe not undergo redeposition onto paper fibers. Instead they are broken down to particle sizes amenable to removal by the normal flotation process under the typical shear conditions found in a paper recycling mill.

Without being restrictive, it is believed that the copolymers of the present invention because they have hydrophilic sugar units (APG maleic acid esters) and hydrophobic synthetic units (vinyl monomers), possess the ability to change surface energy in the aqueous repulping process, allowing adhesive residues to be sheared down to fine non-sticky particles in the range of 10 to 70 μm. As a result, these particles can subsequently be mechanically removed during the flotation deinking process, while deposition on wires, dryer felts and surfaces is minimized. Thus, the copolymers of the present invention are non-tacky under repulping conditions, and they do not undergo redeposition onto paper fibers, but are broken down to particle sizes which are amenable to removal by the flotation process in the setting of typical shear conditions found in a paper recycling mill.

EXAMPLE 1

Free-radical emulsion or suspension copolymerizations were conducted with vinyl monomers and APG maleic acid ester monomers. The emulsion polymerizations were carried out in 1 liter, 4 necked, round bottom reaction kettles equipped with overhead mechanical stirrer, a condenser, a monomer pre-emulsion feed inlet, a thermocouple, an initiator solution feed, a nitrogen purge feed, and a nitrogen bubbler. The reaction vessel was charged with distilled water, stirred at 200 rpm, heated by using a water bath controlled at 80±1° C., and purged with nitrogen. Sodium carbonate buffer and ammonium persulfate initiator were dissolved in water and charged to the reactor immediately before the monomer addition was started. Examples of typical polymerization recipes can be found in Table 3.

TABLE 3

Summary of Select Emulsion Copolymerizations[a]

| | Experiment No. | | | | | | | |
|---|---|---|---|---|---|---|---|---|
| | 317 | 402 | 430 | 625 | 701 | 708 | 724 | 801 |
| Reactor Charge: | | | | | | | | |
| Distilled Water | 112.5 | 112.5 | 159.79 | 59.52 | 59.52 | 59.52 | 59.52 | 59.52 |
| Na$_2$CO$_3$ | 0.25 | 0.25 | 0.50 | 0.26 | 0.26 | 0.26 | 0.26 | 0.26 |
| Ammonium persultate | 0.35 | 0.175 | 0.35 | 0.18 | 0.18 | 0.18 | 0.18 | 0.18 |
| Monomer Pre-Emulsion Feed: | | | | | | | | |
| Sugar-Based Vinyl Monomer (SBV) as Prepared In Example No. | 2 | 3 | 4 | 5 | 6 | 6 | 6 | 7 |
| SBV Monomer | 18.15[b] | 19.37[b] | 59.27[b] | 37.78 | 10.6 | 19.08 | 19.6 | 10.6 |
| Butyl Acrylate | 0 | 43.32 | 65.75 | 29.37 | 68.89 | 37.42 | 71.55 | 71.55 |
| Methyl Methacrylate | 0 | 43.32 | 86.98 | 38.85 | 26.51 | 49.5 | 0 | 0 |
| Vinyl Acetate | 87.85 | 0 | 0 | 0 | 0 | 0 | 23.85 | 23.85 |
| Distilled Water | 35.5 | 35.5 | 71 | 55 | 55 | 55 | 55 | 55 |
| Surfactant | 3.47 | 5.41 | 13.31 | 6.66 | 6.66 | 6.66 | 6.66 | 6.66 |
| Initiator Feed: | | | | | | | | |
| Distilled Water | 10 | 10 | 30 | 15 | 15 | 15 | 15 | 15 |
| Ammonium Persulfate | 0.5 | 0.5 | 3 | 0.75 | 0.75 | 0.75 | 0.75 | 0.75 |
| wt % SBV Monomer (dry basis) | 17[b] | 18[b] | 28[b] | 36 | 10 | 18 | 10 | 10 |
| wt % Solids (aqueous copolymer emulsion) | 40 | 40 | 45 | 45 | 45 | 45 | 45 | 45 |

[a]) Unless otherwise noted all values are in grams
[b]) Includes alkyl maleate monomer used as a solvent in the synthesis of the SBV monomer Monomer pre-emulsions or suspensions were prepared as follows. An APG maleic acid ester monomer composition, for which the preparation is given in subsequent Examples (with corresponding Example numbers given in Table 3), was added to conventional acrylate and/or vinylacetate monomers and mixed thoroughly. The mixture was subsequently added slowly to a distilled water and surfactant solution, while stirring continuously, to form an oil in water emulsion. The monomer pre-emulsion feed was placed in a 500 mL, 3 necked, round bottom flask. Two of the openings were used for a nitrogen purge inlet and outlet and the third neck was fitted with a tube that drew the feed out by an LMI Milton Roy metering pump and into the polymerization vessel. The total monomer feed time was 2.5 hours. The monomer emulsion or suspension was continuously stirred using a magnetic stirbar throughout the feeding process and no phase separation was noticed. A distilled water and ammonium persulfate initiator solution was added continuously to the polymerization reactor for 3.5 hours using a Harvard Apparatus syringe pump. Just before addition of the monomer pre-emulsion was started, the nitrogen purge to the polymerization vessel was shut off, the outlet to the nitrogen bubbler was closed, and an 18 gauge needle was introduced in the rubber septum to maintain atmospheric pressure in the polymerization vessel during the addition of monomer pre-emulsion. This ensured that a nitrogen head was maintained and that the product did not crust on the wall of the reactor vessel. During the polymerization, 1 mL samples were taken for pH and % solids data as a function of time. The % solids were converted into % conversion data which showed the overall conversion and confirmed that starve-fed conditions were achieved. The appearance, color, scent, viscosity, stability, reflux, and bath and reactor temperatures were also recorded throughout the polymerization reaction. The latex was heated for an additional 4.5 hours after all of the initiator had been added. At the end of the 8 hour polymerization period, the reaction mixture was cooled and filtered through a 100 mesh filter. Stable copolymer products were obtained with narrow particle size distributions within the range of 100 to 1000 nm. The usual variations of particle size with soap and monomer concentrations applied. Typical monomer conversions were 95 to 100%.

EXAMPLE 2

A maleic acid ester of an APG was prepared as follows. To a 1 L erlenmeyer flask, containing a magnetic stir bar, was added 185.1 g anhydrous n-butanol (Aldrich, 99.8%), 36.1 g n-octanol (Aldrich, 99+%), and 2.0 g deionized water. To the stirred mixture, 0.184 g (100 mL) of concentrated sulfuric acid (J. T. Baker, 96.6%) was added using a 1 mL glass syringe. This mixture was added to a 500 mL three necked round bottom flask containing 50.0 g of anhydrous α-D-glucose (Aldrich, 96%) and a concave magnetic stir bar. The flask was fitted with a thermocouple probe, a dry air intake, and a 25 mL Barrett receiver on which two glass condensers were mounted, which were connected to a gas bubbler. The condensate collection side of the Barrett receiver was filled with n-heptane, and the gas flow-through side was wrapped in cotton wool for the purpose of insulation. Dry air, passed over a 10 inch column filled with dry molecular sieves and Drierite, was passed through the liquid phase in the round bottom flask. The flask was heated for 4 hours at about 95 to 100° C. using a temperature controlled oil bath. Approximately 12 mL of condensate water was collected in the Barrett receiver as a result of glucose oligomerization reaction and the aldol condensation reaction to give alkylation at the C1 position. The white suspension of sugar particles disappeared as the reaction from glucose to APG proceeded until a clear solution was obtained. This demonstrated that the APG is soluble in the alcohol. The resulting APG solution was colorless, indicating that byproduct formation of colored bodies, such as furfurals, was minimized.

The APG solution was neutralized with 2.0 mL of a 7.30 g/100 mL solution of sodium hydroxide in deionized water. The excess butanol was removed by vacuum distillation at 70 to 105° C. and 22 to 25 inches of Hg. Analysis of the distillate by 500 MHz $^1$H nuclear magnetic resonance (NMR) spectroscopy showed that no detectable levels of octanol had distilled over. The degree of oligomerization, $DP_n$, of the APG was determined to be 1.65 by 500 MHz $^1$H NMR.

To a 100 mL addition funnel wrapped with heating tape, 71.35 g maleic anhydride (Sigma, 99+%) was added, a thermocouple was inserted, and the funnel was heated to 60 to 85° C. until all the maleic anhydride powder was melted. The liquid maleic anhydride was added over a period of about 10 minutes to the APG/octanol mixture which was at an initial temperature of about 100° C., resulting in an exotherm up to about 120° C. After 1 hour, the reaction was cooled to 50° C., and 162.8 g of n-hexanol (Aldrich, 98%) and about 50 g of dry molecular sieves was added for the esterification of free maleic acid groups. The esterification reaction was allowed to proceed for 12 hours at approximately 120° C. The reaction product was cooled and divided into two equal portions; to one of the portions 0.64 g of the titanium-based esterification catalyst "TYZOR" TBT Titanate (Du Pont Chemicals) was added; the mixture was reheated and allowed to react for an additional 12 hours. Excess hexanol was removed using a rotary evaporator. Samples were taken for analysis by NMR and thin layer chromatography, which confirmed the formation of APG, APG-maleic acid/octyl maleic acid mixture, and the APG-maleic/octyl maleic ester product in the respective reaction steps. 500 MHz $^1$H NMR analysis of the key fractions, which were eluted using silica gel (Aldrich, Grade 923, 100–200 mesh) column chromatography, further confirmed the formation of the APG-maleic acid ester product. The pH of the APG-maleic acid/octyl maleic acid mixture was about 1.8, while the pH of the APG-maleic/octyl maleic ester product was 6.3 and 6.8 for the two fractions prepared in the absence and in the presence of the esterification catalyst, respectively.

EXAMPLE 3

The procedure given in Example 2 was followed. The reaction time to form the APG was 3 hours, 20 minutes. The $DP_n$ of the APG was determined to be 1.67. Instead of 71.35 g maleic anhydride, 75.90 g was used, and 200.0 g of anhydrous n-butanol was used in the esterification step in place of n-hexanol; 0.75 g of the "TYZOR" TBT catalyst was used, and 89 g of dry basic alumina in place of molecular sieves. Excess butanol was removed using a rotary evaporator. Samples were taken for analysis by NMR and thin layer chromatography, which confirmed the formation of APG, APG-maleic acid/octyl maleic acid mixture, and their partial esterification products. The pH of the APG-maleic acid/octyl maleic acid mixture was about 1.8, while the pH of the final product was 2.6.

EXAMPLE 4

A maleic acid ester of an APG was prepared as follows. To a 1 L erlenmeyer flask, containing a magnetic stir bar, was added 411.4 g n-butanol (Mallinckrodt; 99.7%, 0.03% $H_2O$), and to the stirred mixture, 0.368 g (200 ml) of concentrated sulfuric acid (J. T. Baker, 96.6%) was added using a 1 mL glass syringe. This mixture was added to a 1 L three necked round bottom flask containing 111.3 g of α-D-glucose (containing 8.8% water) and a concave magnetic stir bar. The flask was fitted with a thermocouple, a dry air intake, a Barrett receiver and two glass condensers as described in Example 2. The flask was heated for 3 hours, 25 minutes at about 95 to 102° C. Approximately 18 mL of condensate water was collected in the Barrett receiver. The white suspension of sugar particles disappeared as the reaction from glucose to APG proceeded until a clear solution was obtained. The resulting APG solution was colorless. The APG solution was neutralized with 1.0 mL of a 29.2 g/100 mL solution of sodium hydroxide in deionized water. The $DP_n$ of the APG was determined to be 1.59 by 500 MHz $^1$H NMR. 77.5 g of dibutyl maleate (Aldrich, 99.7%) was added to the APG-butanol solution. The excess butanol was removed by vacuum distillation at 75 to 105° C., and 26 to 29 inches of Hg. The APG was soluble in dibutyl maleate at temperatures above about 95° C. Analysis of the distillate by $^1$H NMR showed that no detectable levels of dibutyl maleate had distilled over.

To a 250 mL addition funnel wrapped with heating tape, 110.24 g maleic anhydride (Sigma, 99+%) was added, a thermocouple was inserted, and the funnel was heated to 60 to 85° C. until all the maleic anhydride powder was melted. The liquid maleic anhydride was added over a period of about 13 minutes to the APG/dibutyl maleate mixture which was at the initial temperature of about 106° C., resulting in an exotherm up to about 120° C. The total reaction time was 4 hours. Samples were taken for analysis by NMR and thin layer chromatography, which confirmed the formation of APG, and the complete conversion of APG to maleated APG in the respective reaction steps.

EXAMPLE 5

The procedure given in Example 4 was followed using 411.6 g n-butanol (Aldrich, anhydrous, 99.8%), and 2.0 g additional water, 100.24 g anhydrous α-D-glucose. The APG reaction time was 3 hours, and the $DP_n$ of the APG was determined to be 1.66. No dibutyl maleate was added prior to distillation of the alcohol. After removal of the excess butanol, the butyl glycoside thus produced was a viscous liquid. For the maleation reaction, 109.89 g maleic anhydride was used, which was added in less than 1 minute to facilitate stirring. The reaction temperature at the start of the reaction was 77° C., and an exotherm was observed up to about 117° C. The total reaction time was 4 hours. Samples were taken for analysis by NMR and thin layer chromatography, which confirmed the formation of APG, and the complete conversion of APG to maleated APG in the respective reaction steps.

EXAMPLE 6

The procedure given in Example 5 was followed using 411.8 g n-butanol (Aldrich, anhydrous, 99.8%), 2.0 g additional water, and 100.02 g anhydrous α-D-glucose. The APG reaction time was 3 hours, and the $DP_n$ of the APG was determined to be 1.64. For the maleation reaction, 108.58 g maleic anhydride was used.

EXAMPLE 7

The procedure given in Example 5 was followed using 411.4 g n-butanol (Aldrich, anhydrous, 99.8%), 2.0 g additional water, and 100.1 g anhydrous α-D-glucose. The APG reaction time was 3 hours. For the maleation reaction, 109.0 g maleic anhydride was used. The reaction time for the maleation was 2 hours. Following the maleation reaction, the intermediate product was divided into three portions to which 6, 23 and 76% of NEODOL R 23 (a $C_{12}$–$C_{13}$ mixture of alcohols, Shell Chemical Co., $MW_{ave}$=193) and 50 g of dry basic alumina were added for esterification at 120° C. for the 23 and 76% NEODOL fractions. The reaction time was about 4 hours for the 6% NEODOL fraction and about 15 hours for the other two fractions.

EXAMPLE 8

The novel copolymers of the present invention are non-tacky under repulping conditions, they do not undergo redeposition onto paper fibers and they are broken down to particle sizes which are amenable to removal by the floatation process under typical shear conditions found in a paper recycling mill.

To illustrate the unique repulpability of the copolymers provided herein, the following test procedure was used. To 1 L of a caustic solution (NaOH, pH=10), 4 to 5 grams of a dry adhesive polymer film was added, and the mixture was blended at 65° C. for 5 minutes using a Waring Blender at the grate setting. Samples were taken from the foam and liquid phase, and examined under a phase contrast microscope at 100× and 1000× magnifications. Examination of the foam showed that the foam was enriched in adhesive particles in the size range of 10 to 70 $\mu$m. This served as a convenient method for examining the mass transfer of adhesive particles between the liquid and foam phases, a process well known to those skilled in the art of flotation deinking. Photomicrographs were taken at both magnifications for various adhesive compositions provided in this invention, and their performance was compared with control adhesive compositions which contained no sugar-based vinyl monomer, as described in Table 4.

TABLE 4

| | Composition of Various Adhesives used in Testing Repulpability[a] | | | |
|---|---|---|---|---|
| Sample No. | 1 | 2 | 3 | 4 |
| Adhesive Type[b] | PSA Control | non PSA Control | PSA | Non PSA |
| Sugar-Based Vinyl Monomer (SBV) | 0 | 0 | 10 | 10 |
| Butyl Acrylate (BA) | 72 | 43 | 65 | 39 |
| Methyl Methacrylate (MMA) | 28 | 57 | 25 | 51 |
| BA/(BA + MMA) Ratio | 0.72 | 0.43 | 0.72 | 0.43 |

[a]All values are expressed in % w/w
[b]PSA = pressure sensitive adhesive

Photomicrographs (at 100× magnification) of the liquid phase for Sample no. 3 (Table 4), which is an example of a pressure-sensitive adhesive made with a monomer of the present invention, showed particles in the range of 20 to 200 um in diameter. In the control experiment, a dry adhesive film was treated in the same manner, using a pressure sensitive adhesive of similar composition which did not contain a sugar-based monomer (Sample no. 1, Table 4). In contrast to Sample no. 3, the dry adhesive film of Sample no. 1 became sticky in the blender, and no small particles were observed under the microscope at either 100× or 1000× magnification for this control sample. These results demonstrate that the adhesive which was copolymerized using the APG maleic acid ester monomer is more susceptible to break down to particles under the shear forces generated in the blender.

Similar results were observed for a non-pressure sensitive adhesive sample (Sample no. 4). This copolymer also sheared down to small particles, which were in the range of 10 to 100 $\mu$m. The non-pressure sensitive control (Sample no. 2) was sheared down to particles greater than 100 $\mu$m. This size range is considerably larger than that was observed for Sample no's 3 and 4, which employed copolymer of the present invention.

The results of Example 8 illustrate that pure pressure sensitive or non pressure sensitive adhesive resins containing the copolymers of the present invention, have the unique property of being broken up into small particles in a blender even in the absence of paper fiber.

EXAMPLE 9

To better simulate the conditions found in a paper recycling mill, where such adhesives are present as coatings on paper, a model repulping experiment was conducted. This model experiment characterizes the fate of such adhesive residues in the presence of paper fiber. A variation of Example 8 was conducted to test the effects of shear conditions on model repulping experiments, in which such adhesives are present as coatings on Kraft paper.

The conditions of the experiment were as follows: 4.0 grams of wet adhesive (latex) (Sample No. 3) were applied to a sheet of blotter paper (15 grams). This preparation was dried overnight and subsequently cut into 1.5 cm×1.5 cm squares. The paper squares were added to 500 mL of water, adjusted to pH=10 with NaOH, and blended in a Waring Blender for 5 minutes at 65° C. The resultant pulp slurry was examined under a phase contrast microscope at 100× magnification and 1000× magnification. The adhesive particles were shown to range in size from 3 to 30 $\mu$m. This represents a shift to lower particle size as compared to the particle size range in the repulping experiments where no Kraft fiber was present. This is due to the increase in effective shear forces generated in the blender when pulp fibers are present.

Adhesive particles were observed to adhere to the edge of air bubbles for samples taken from the foam or aqueous layers. This was routinely observed and demonstrates that the adhesive particles are relatively hydrophobic in nature. Hydrophobicity is a basic requirement for physisorption of particles onto an air bubble, which is well known to those skilled in the art.

These results demonstrate that adhesives containing the copolymers of the present invention are susceptible to breakdown by the shear forces generated in the blender, and that the size distribution of adhesive residues is in the range which is amenable to removal by flotation.

The products of the present invention provide new sugar-based copolymers utilizing agricultural resources which can be returned to those resources in an environmentally sound manner. The invention provides new polymeric materials for environmental compatibility. This was achieved by designing and engineering repulpable and biodegradable materials that are polymeric, yet break down under appropriate process conditions. Thus, the copolymers of the present invention facilitate the recycling of paper because they are sheared down into small particles in the paper recycling process. This allows the adhesive residues to be removed the process water via the flotation deinking facility of a paper recycling mill. On the other hand, for disposable packaging applications, these sugar-based vinyl copolymers can be assimilated by microorganisms under composting conditions to help convert biodegradable waste into compost.

The invention has been described in an illustrative manner, and it is to be understood the terminology used is intended to be in the nature of description rather than of limitation.

Many modifications and variations of the present invention are possible in light of the above teachings. Therefore, it is to be understood that within the scope of the appended claims, the invention may be practiced otherwise than as specifically described.

What is claimed is:

1. A polymerizable alkyl polyglycoside maleic acid ester which has the formula:

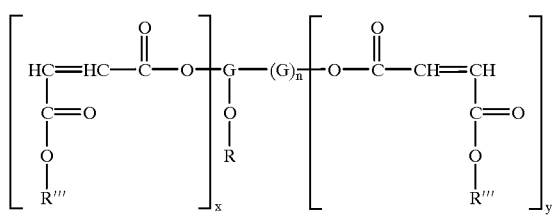

wherein G is a saccharide moiety; R is selected from the group consisting of a C1 to C30 alkyl; R'" is selected from the group consisting of hydrogen, a C1 to C30 alkyl or a mixture thereof, n is an integer of 0 to 10; x and y are integers of 0 to 3 or 0 to 4, where the maximum value of 3 or 4 for x and y equals the number of hydroxyls on the G moiety, but not both x and y are zero.

2. A compound of claim 1 wherein G is derived from α-D-glucose.

3. A compound of claim 1 wherein R is selected from the group consisting of a C3 to C8 alkyl or a mixture thereof.

4. A compound of claim 1 wherein R'" is selected from the group consisting of hydrogen, a C8 to C18 alkyl group or a mixture thereof.

5. A compound of claim 1 which is prepared by esterification of alkyl polyglycoside maleic acid with a primary C1 to C30 alcohol or a mixture thereof.

6. A method of preparing a compound of claim 1 which comprises reacting an alkyl polyglycoside with maleic acid anhydride under anhydrous reaction conditions using maleic anhydride as both a solvent and a reactant.

7. A method of claim 6 wherein the molar stoichiometry of maleic acid anhydride to alkyl polyglycoside is more than one.

* * * * *